United States Patent [19]

Arzbaecher et al.

[11] Patent Number: 4,817,611
[45] Date of Patent: Apr. 4, 1989

[54] ESOPHAGEAL ELECTROCARDIOGRAPHY ELECTRODE

[75] Inventors: Robert C. Arzbaecher, Chicago; D. J. Davis, Jr., Wheaton; Mark P. Lowther, Barrington; all of Ill.

[73] Assignee: Arzco Medical Electronics, Inc., Chicago, Ill.

[21] Appl. No.: 930,748

[22] Filed: Nov. 13, 1986

[51] Int. Cl.⁴ .......................... A61B 5/04; A61N 1/05
[52] U.S. Cl. ..................................... 128/642; 128/784
[58] Field of Search ................ 128/631, 642, 784–786, 128/788

[56] References Cited

U.S. PATENT DOCUMENTS

| | | |
|---|---|---|
| 164,184 | 6/1875 | Kidder . |
| 1,042,624 | 10/1912 | Wagoner .............. 128/788 |
| 1,056,336 | 3/1913 | Hurdman . |
| 3,326,207 | 6/1967 | Egan . |
| 3,339,542 | 9/1967 | Howell . |
| 3,348,548 | 10/1967 | Chardack ............ 128/786 |
| 3,403,684 | 10/1968 | Stiebel et al. ......... 128/788 |
| 3,703,900 | 11/1972 | Holznagel . |
| 3,716,059 | 2/1973 | Welborn et al. . |
| 3,800,800 | 4/1974 | Garbe et al. .......... 128/788 |
| 3,943,938 | 3/1976 | Wexler et al. ......... 128/421 |
| 3,951,136 | 4/1976 | Wall . |
| 4,088,138 | 5/1978 | Diack et al. . |
| 4,090,518 | 5/1978 | Elam . |
| 4,176,660 | 12/1979 | Mylrea et al. . |
| 4,236,529 | 12/1980 | Little ................ 128/786 X |
| 4,304,239 | 12/1981 | Perlin . |
| 4,304,240 | 12/1981 | Perlin . |
| 4,349,030 | 9/1982 | Belgard et al. . |
| 4,351,330 | 9/1982 | Scarberry . |
| 4,432,375 | 2/1984 | Angel et al. . |
| 4,467,813 | 8/1984 | Schomburg . |
| 4,473,078 | 9/1984 | Angel . |
| 4,475,555 | 10/1984 | Linder . |
| 4,476,872 | 10/1984 | Perlin . |
| 4,517,984 | 5/1985 | Perlin . |
| 4,574,807 | 3/1986 | Hewson et al. . |
| 4,640,298 | 2/1987 | Pless et al. . |
| 4,683,890 | 8/1987 | Hewson . |
| 4,706,688 | 11/1987 | Michael et al. . |
| 4,729,384 | 3/1988 | Bazenet . |
| 4,735,206 | 4/1988 | Hewson . |

FOREIGN PATENT DOCUMENTS 121090 2/1972 Denmark .
133400 1/1979 Fed. Rep. of Germany .

OTHER PUBLICATIONS

Clinical Use of an Esophageal ECG Electrode During Surgery, Anesthesia and Analgesia, vol. 44, No. 1, 1964 by Kavan and Colvin.
An Esophageal Multiprove for Temperature, Electrocardiogram, and Heart and Lung Sounds Measurements, 1978 IEEE, vol. BME-25 by Demer et al.
Telecor, Model 6003, published by Medtronic, Inc.
Esophageal Monitoring Probes published by Diagnostic Instrument Corporation.
Trans-Esophageal Pacing by Andersen and Pless was published Jul.-Aug. 1983 by Futura Publishing Company, Inc.
Trans-Oesophageal Dual-Chamber Pacing by Andersen and Pless published in the International Journal of Cardiology, May, 1984.
Experience with an Electrical Conductive Rubber Electrode for Esophageal Pacing in Infants by Meisner et al. (EXCERPTA MEDICA).
An Esophageal Balloon Electrode for Cardiac Pacing by Mitsui, Tanaka and Saigusa in Cardiac Pacing, published by Van Goram, 1973.
Robert Arzbaecher, "A Pill Electrode for the Study of Cardiac Arrhythmia" (1978), Medical Instrumentation, 12; 277-281.
Jenkins et al., "Use of the Pill Electrode for Transesophageal Atrial Pacing" (1985), PACE, 8; 512-527.
Catalog page Arzco Medical Electronics, Inc., no page No., Entitled "The Pill-Electrode for Esophageal Electrocardiography"

Primary Examiner—Lee S. Cohen
Attorney, Agent, or Firm—Dressler, Goldsmith, Shore, Sutker & Milnamow, Ltd.

[57] ABSTRACT

An integrally formed, molded, esophageal electrode provides for positive locking of spaced-apart conducting members to the body section. The electrode includes a molded body section with a centrally formed shoulder. The shoulder provides for spacing between the two cylindrical conducting members carried on the body of the electrode. Molded hemispherical end members provide positive locking of the conductive members to the body portion.

18 Claims, 2 Drawing Sheets

ESOPHAGEAL ELECTROCARDIOGRAPHY ELECTRODE

FIELD OF THE INVENTION

The invention pertains to devices and methods suitable for use in connection with esophageal electrocardiography. More particularly, the invention pertains to an improved electrode structure and method of making same useable as either a sensor for esophageal electrocardiography or a transducer for electrical stimulation.

BACKGROUND OF THE INVENTION

It has generally been known that cardiac stimulation can be carried out by means of external electrodes positioned against the chest and back of a patient. One such system has been disclosed in U.S. Pat. No. 4,349,030 to Belgard et al. entitled "External Noninvasive Electric Cardiac Stimulation."

It has also been generally known, as an alternate to the use of exterior electrodes placed on the body of a patient, to position swallowable electrodes in the esophagus at the level of the atria. Such esophageal electrodes have been disclosed in various articles such as "*A Pill Electrode For The Study of Cardiac Arrhythmia*", R. Arzbaecher, Medical Instrumentation Vol. 12 - No. 5, 1978; and "*Use of the Pill Electrode for Transesophageal Atrial Pacing*", Jenkins et al., PACE Vol. 8, July-August 1985.

Notwithstanding their utility and success, the prior art esophageal electrodes have been formed from separate components mechanically assembled together into a completed electrode. There continues to be a need for an electrode with all components inseparatably bonded together in such a form that the device can be inserted and removed with little or no abrasion or trauma to the esophagus of the patient.

A disadvantage of the known electrodes is that the tolerance of the extruded TEFLON ® tubing used therein can not be adequately controlled. As a result, there is an inordinate amount of wasted tubing. This also translates into labor wasted in unsuccessful attempts to assemble the device.

SUMMARY OF THE INVENTION

In accordance with the invention, an improved esophageal electrode is provided with a molded body portion having two hemispherical end regions. The hemispherical end regions retain two spaced apart conducting members on the body portion.

In one embodiment of the invention, the electrode can be formed with a method which utilizes two molding steps. In this embodiment, an internal plastic electrode fixture is first formed. The fixture is generally cylindrical shaped with an opening therethrough. Pick-up wires are located on the ends of the fixture with one of the wires passing through the central opening of the fixture. Metal sleeves are slid onto the ends of the fixture and abut a central cylindrical region in spaced apart relationship. This structure is placed in a mold and plastic, such as polyethylene, is injected into the central region of the fixture under pressure. The central region and the hemispherical end regions are then filled to lockingly retain the cylindrical metal members on the electrode.

In an alternate embodiment, the electrode can be formed by placing two cylindrical metal members in spaced apart relationship in a mold formed with two curved end regions. Each of the cylindrical metal members has a conductive wire affixed thereto. The mold can be closed and the interior region thereof filled with plastic under pressure. A solid, one piece electrode is thus formed with the two spaced apart cylindrical metal members permanently affixed thereto.

In a preferred form of the invention, the electrode can be formed using stainless steel cylindrical metal members. Alternately, brass could be used. The wires can be formed of stainless steel with a TEFLON ® coating.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE PREFERRED EMBODIMENTS

Figure 1:
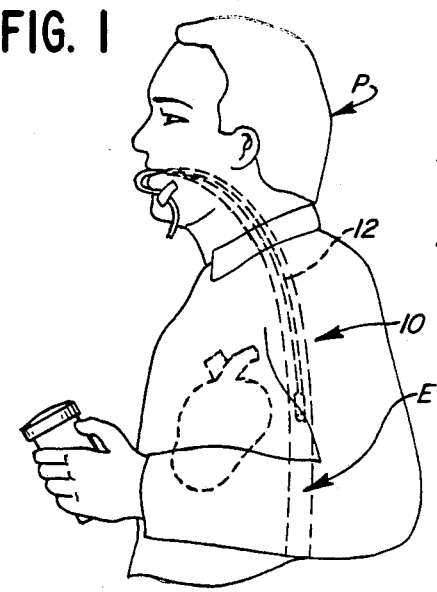
FIG. 1 is a schematic side view of a patient illustrating an esophageal electrode positioned in the esophagus.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 illustrates a patient P with an esophagus E. The patient has swallowed an esophageal electrode 10 which is position in the esophagus E at the level of the atria. The electrode 10 is coupled by wires 12, which pass up through the esophagus and out the patient's mouth, to external equipment.

Figure 2:
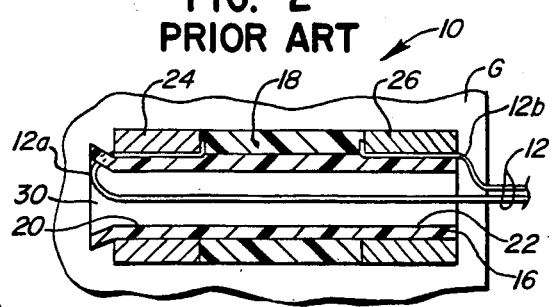
FIG. 2 is a side view in section of a known prior art esophageal electrode.

FIG. 2 illustrates a sectional view of a known esphageal electrode which could correspond to the electrode 10. The structure of FIG. 2 includes an inner elongated extruded tubing member 16 on which is positioned, centrally located, a second tubing member 18. The members 16 and 18 could both be formed of extruded TEFLON ® tubing.

Positioned on the distal and proximal ends 20 and 22 respectively of the tubing member 16 are stainless steel cylindrical bands 24 and 26. The bands 24 and 26 are spaced apart sensors when the electrode 10 is used for monitoring purposes. Alternately, when the electrode 10 is used for esophageal pacing the cylindrical metal members 24 and 26 are a source of electrical signals to carry out the pacing function.

The centrally located preformed tubing member 18 keeps the metal numbers 24 and 26 spaced apart a desired distance. Wires 12a and 12b have ends which are clamped beneath the cylindrical metal members 24 and 26 and are held in place on the electrode 10 by frictional forces.

A portion 30 of the distal end region 20 is outwardly flared slightly to provide a mechanical lock such that the cylindrical metal member 24, the centrally located tubing member 18 and the cylindrical metal member 26 can be slide off of the body portion 16. The electrode 10 is conventionally encapsulated in gelatine G to improve the ease of swallowing.

Figure 3:
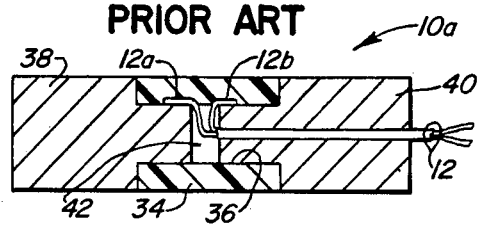
FIG. 3 is a side view in section of yet another known esophageal electrode.

FIG. 3 illustrates an alternate known structure 10a of an esophageal electrode. The electrode 10a is formed with a central cylindrical extruded tubing, such as TEFLON ®, body portion 34. The body portion 34 is hollow with an interior cylindrical region 36. Metal members 38 and 40 are forced into the ends of the region 36 in spaced apart relationship such that there is a space 42 therebetween. Wires 12a and 12b are clamped between the respective metal members 38 and 40 in the interior region 36 of the TELFON ® sleeve 34.

Figure 4:
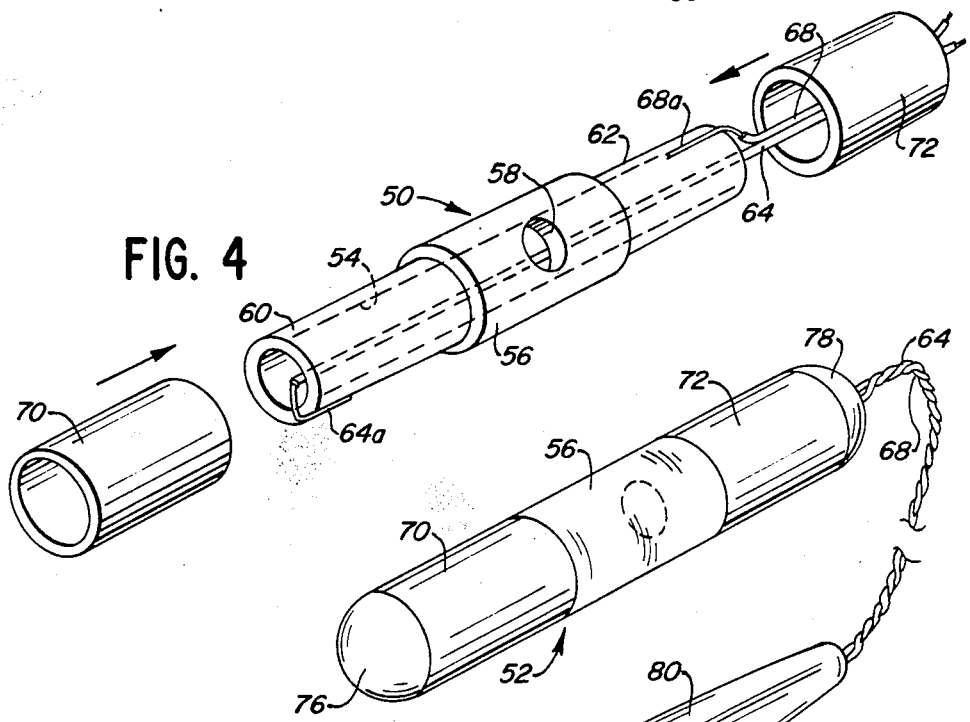
FIG. 4 is a plan view of an electrode fixture in accordance with the present invention.
Figure 5:
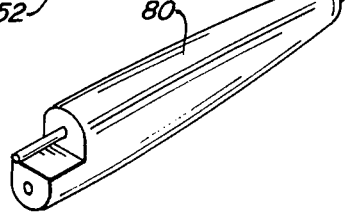
FIG. 5 is a plan view of an esophageal electrode in accordance with the present invention.

FIG. 4 illustrates an electrode fixture 50 useable to form a new esophageal electrode structure 52. The fixture 50 has an overall cylindrical shape with a hollow region 54 therein. A central and cylindrically shaped region 56 is formed with an opening 58 into the interior region 54. Extending axially from the central region 56 are two cylindrical regions 60 and 62 which are integrally formed with the region 56. The regions 60 and 62 are formed with essentially the same radius which is less than the radius of the central region 56.

The electrode fixture 50 can be formed by injection molding. A variety of plastic materials can be used. Polyethylene has been found to be a suitable material. The exact material is not a limitation of the present invention. Any plastic material of a non-toxic variety which can be injection molded would be suitable.

Connection wires 64 and 68 are provided for coupling to the electrode 52. Each of the wires 64 and 68 has a respective bare end 64a and 68a. The respective bare ends 64a and 68a are positioned adjacent the cylindrical end surfaces of the members 60 and 62.

Two stainless steel metal sleeves 70 and 72 are slid onto the spaced-apart cylindrical end members 60 and 62. The sleeves 70 and 72 clamp the respective wire end members 64a and 68a in place and provide a highly reliable electrical connection thereto. The output radius of each of the conducting members 70, 72 matches the outer radius of the central region 56.

The electrode fixture 50 can then be placed in an insert injection mold and plastic can be injected under pressure into the opening 58. The injected plastic fills the interior region 54 and, due to the shape of the mold, forms first and second hemispherical end regions 76 and 78. The regions 76 and 78 along with the central region 56 mechanically lock the metal cylindrical members 70 and 72 in fixed, spaced apart relationship. The wires 64 and 68 can be twisted together and can be terminated in a molded two-conductor connector 80.

The electrode 52 has the advantage that it is formed as a smooth continuous unitary unit which, due to the molded end members 76 and 78, is securely mechanically locked together. In addition, the end member 78 readily slides up the esophageous during the removal phase.

Figure 6A:
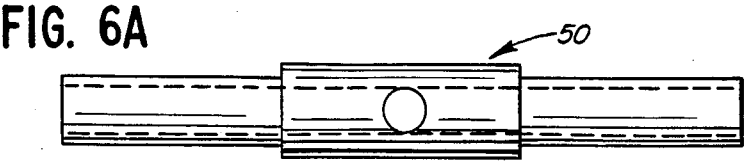
FIGS. 6A-6E illustrate the steps of practicing a method of forming an esophageal electrode in accordance with the present invention.
Figure 6B:
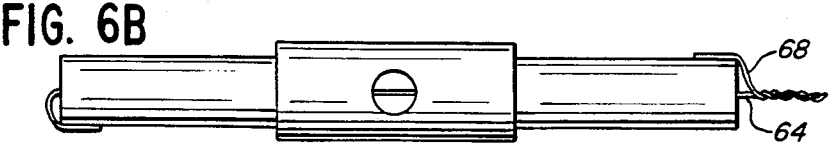
Figure 6C:
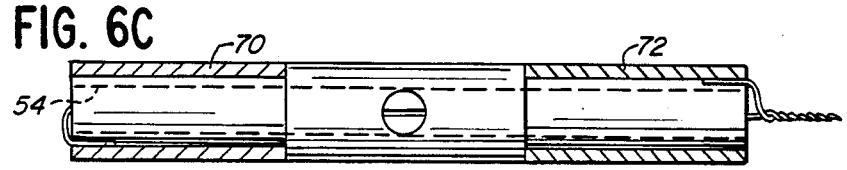

FIGS. 6a-6e schematically illustrate the method of forming the electrode 52. The hollow electrode fixture 50 as described above is first formed in a molding step as in FIG. 6a. As illustrated in FIG. 6b, the wires 64 and 68 are positioned on the ends of the fixture 50. The metal cylindrical members 70 and 72 are illustrated in FIG. 6c after having been slid onto the cylindrical end members 60 and 62 respectively.

Figure 6D:
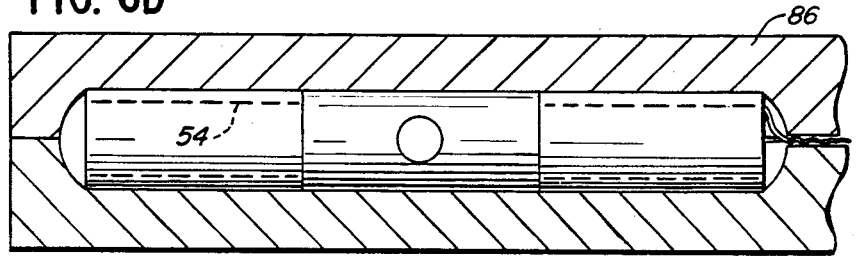
Figure 6E:
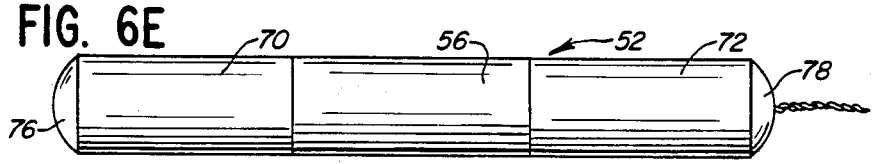

In FIG. 6d the partially completed electrode is positioned in a mold 86. Plastic is injected into the cavity 54 of the fixture 56 thereby forming the hemispherical end regions 76 and 78 and filling the opening 58. The completed electrode 52 is illustrated in FIG. 6e.

The smooth hemispherical end 78 should minimize abrasion and trauma during the withdrawal phase from the patient's esophagus. The electrode 58 can be coated, as is conventional, with gelatin prior to use.

Figure 7:
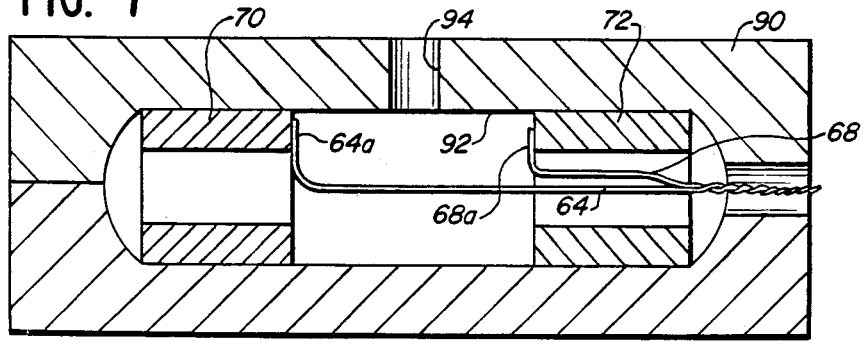
FIG. 7 illustrates an alternate method of forming an esopagheal electrode in accordance with the present invention.

FIG. 7 illustrates and alternate method of forming the electrode 52. In FIG. 7 a mold 90 has an interior cavity 92 in which the spaced apart cylindrical metal members 70 and 72 can be positioned. The wires 64 and 68 can be affixed at the respective ends 64a and 68a by soldering at the respective ends 64a and 68a by soldering or welding to retain them in position temporarily. Plastic then can be injected into the mold 90 through the filling port 94 filling the cavity 92 in a single injection step. The completed electrode can then be removed from the mold 90.

The overall length of the present electrode is on the order of 0.875 inches (2.33 cm). The conducting cylindrical members are each on the order of 0.25 inches (0.64 cm). The diameter of the electrode is on the order of 0.125 inches (0.32 cm).

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. An electrode suitable for swallowing by a patient comprising:

an elongated, molded, non-conducting body member, said body member being generally cylindrically-shaped, with a centrally located radially extending shoulder, said shoulder having an essentially cylindrical, exterior, peripheral surface;

first and second electrical conductors, each said conductor formed as a thin-walled, hollow cylinder said conductors carried by said body member spaced apart thereon so as to abut first and second ends of said shoulder;

said body member having first and second conductor locking end regions with each said end region having a generally curved exterior shape and with said locking end regions formed joined together as a single unitary member;

first and second elongated wire conducting members with each said wire conducting member electrically coupled to a respective conductor with a selected one of said wire conducting members extending, at least in part, substantially axially through said body member.

2. An electrode as in claim 1 with the first and second end regions each disposed adjacent an end of a respective one of the first and second electrical conductors at a respective position that is separated from said shoulder by the respective lengths of the first and second electrical conductors.

3. An electrode as in claim 2 with said electrical conductors formed of stainless steel.

4. An electrode as in claim 2 with said body member molded of polyethylene.

5. An electrode as in claim 4 with said wire conducting members terminating in an electrical socket.

6. An electrode as in claim 5 with said electrical sock formed with a molded body portion.

7. An electrode as in claim 1 with each said conducting member having a proximal end and a distal end with each said distal end having a selected bend with said shoulder having end sides with each said end side thereof disposed adjacent a said bend of a respective one of the first and the second electrical conductors.

8. An esophageal electrode comprising:
a molded, unitary, elongated body member with a central cylindrical region having a first diameter and spaced apart ends,
first and second cylindrical extension regions attached to respective of said spaced-apart ends, each said cylindrical extension region having a second diameter, less than said first diameter,
first and second hemispherical end regions attached to one another and positioned adjacent to respective of said extension regions with said end regions each having a diameter substantially equal to said first diameter;
a first and a second electrically conductive tubular member, each exhibiting an internal diameter substantially equal to the second diameter and exhibiting an external diameter substantially equal to the first diameter, each mounted upon a respective one of the two extension cylindrical regions and extending for the length thereof and held in its mounted position by a respective one of the end regions; and
first and second elongated means for electrical conduction electrically connected to respective ones of the first and the second electrically conductive tubular members.

9. An esophageal electrode comprising:
a molded, unitary, elongated body member with a central cylindrical region having a first diameter and spaced apart ends,
first and second cylindrical extension regions attached to respective of said spaced-apart ends, each said cylindrical extension region having a second diameter, less than said first diameter,
first and second hemispherical end regions positioned adjacent to respective of said extension regions with said end regions coupled to one another and with each said end region having a diameter substantially equal to said first diameter;
a first and a second electrically conductive tubular member, each exhibiting an internal diameter substantially equal to said second diameter and exhibiting an external diameter substantially equal to said first diameter, each mounted upon a respective one of said two extension cylindrical regions and locked thereon by a respective one of said hemispherical end regions; and
first and second elongated means for electrical conduction electrically connected to respective of the first and the second electrically conductive tubular members.

10. An esophageal electrode comprising:
a molded, unitary, elongated body member with a central cylindrical region having a first diameter and spaced apart ends,
first and second cylindrical extension regions attached to respective of said spaced-apart ends, each said cylindrical extension region having a second diameter, less than said first diameter,
first and second hemispherical end regions carried adjacent to respective of said extension regions with said end regions each having a diameter substantially equal to said first diameter;
a first and a second electrically conductive tubular member, each exhibiting an internal diameter substantially equal to said second diameter and exhibiting an external diameter substantially equal to said first diameter, each mounted upon a one of the two extension cylindrical regions and locked thereon by a respective one of said end regions; and
first and second elongated means for electrical conduction electrically connected to respective ones of said first and said second electrically conductive tubular members with at least one of said elongated means physically separated from the other said elongated means at the region of electrical connection by a substantial thickness of the body member.

11. An esophageal electrode comprising:
an elongated insulative body member having a generally cylindrical shape with an enlarged central region, two extension regions of lesser diameter substantially symmetrically coupled to the central region, and two enlarged end regions carried substantially symmetrically adjacent the extension regions and coupled to one another through the body member;
first and second electrical conductors, formed as hollow cylinders of an internal diameter complementary to the body member's extension regions, positioned upon respective of the extension regions and held thereon between respective of the enlarged end regions and the enlarged central region; and
first and second elongated wires at least one of which has an end which is routed substantially axially and centrally into one extension region of the body member, the wires being coupled electrically to respective of said conductors.

12. An esophageal electrode comprising:
a molded, elongated body member with a central cylindrical region having a first diameter and spaced apart ends;
first and second cylindrical extension regions located adjacent to respective of said spaced-apart ends, each said cylindrical extension region having a second diameter, less than said first diameter;
first and second rounded end regions attached to one another and positioned adjacent to respective of said extension regions with said end regions each having a diameter substantially equal to said first diameter;
a first and a second electrically conductive tubular member, each having an internal diameter substantially equal to the second diameter and having an external diameter substantially equal to said first diameter, each said member mounted upon a respective one of said two cylindrical extension regions and extending for the length thereof and held in its mounted position by a respective one of said end regions; and first and second elongated means for electrical conduction electrically connected to respective ones of the first and the second electrically conductive tubular members.

13. An esophageal electrode comprising:

a molded, elongated body member with a central cylindrical region having a first diameter and spaced apart ends;

first and second cylindrical extension regions with each said region extending from said body member adjacent to respective of said spaced-apart ends, each said cylindrical extension region having a second diameter, less than said first diameter;

first and second rounded end regions positioned adjacent to respective of said extension regions with said end regions coupled to one another and with each said end region and having a diameter substantially equal to said first diameter;

a first and a second electrically conductive tubular member, each exhibiting an internal diameter substantially equal to said second diameter and exhibiting an external diameter substantially equal to said first diameter, each mounted upon a respective one of said two cylindrical extension regions and locked thereon by a respective one of said rounded end regions; and first and second elongated means for electrical conduction electrically connected to respective of the first and the second electrically conductive tubular members.

14. An esophageal electrode comprising:

a molded, elongated body member with a central cylindrical region having a first diameter and spaced apart ends;

first and second cylindrical extension regions located adjacent to respective of said spaced-apart ends, each said clindrical extension region having a second diameter, less than said first diameter;

first and second rounded end regions carried adjacent to respective of said extension regions with said end regions each having a diameter substantially equal to said first diameter;

a first and a second electrically conductive tubular member, each exhibiting an internal diameter substantially equal to said second diameter and exhibiting an external diameter substantially equal to said first diameter, each mounted upon a one of the two cylindrical extension regions and locked thereon by a respective one of said end regions; and first and second elongated means for electrical conduction electrically connected to respective ones of said first and said second electrically conductive tubular members with at least one of said elongated means physically separated from the other said elongated means at the region of electrical connection by a substantial thickness of the body member.

15. An esophageal electrode comprising:

an elongated insulative body member having an enlarged central region with a generally cylindrical shape with a first diameter and with two extension regions each of lesser diameter substantially symmetrically extending from said body member on a common center-line and two enlarged end regions carried substantially symmetrically adjacent said extension regions and coupled to one another first and second electrical conductors, formed as hollow cylinders of an internal diameter corresponding to said diameter of said extension regions, said conductors positioned upon respective of said extension regions with each said conductor held thereon between respective of said enlarged end regions and said enlarged central region; and first and second elongated wires at least one of which has an end which is routed substantially axially and centrally into one of said extension regions said wires being coupled electrically to respective of said conductors.

16. An esophageal electrode comprising:

a molded, unitary, elongated insulative body member with a cylindrical central region having a first diameter with an extension region of lesser diameter symmetrically extending on each side of said body member and terminating in a hemispherical end whose diameter substantially equals said first diameter of said body member;

first and second electrical conductors, formed as hollow cylinders of an internal diameter corresponding to said extension regions of said body member and an external diameter corresponding to said first diameter of said body member, said conductors securely positioned upon respective of said extension regions between said central region of said body member and a respective one of said hemispherical ends; and first and second elongated wires, at least one of which has an end which is routed substantially axially and centrally within said body member with each said wire being coupled electrically to a respective one of said electrical conductors at a location adjacent a surface of said respective extension region.

17. An electrode as in claim 16 with said elongated wires routed, at least in part, substantially axially and internally of said body member, each said wire being coupled electrically to a respective region of one of said respective electrical conductors.

18. An electrode as in claim 16 with said elongated wires terminating in an electrical socket formed with a molded body portion.

* * * * *